United States Patent [19]

Shettigar

[11] Patent Number: 5,464,535
[45] Date of Patent: Nov. 7, 1995

[54] FILTER FOR ON-LINE PLASMA SAMPLING

[75] Inventor: Udipi R. Shettigar, Salt Lake City, Utah

[73] Assignee: University of Utah, Salt Lake City, Utah

[21] Appl. No.: 220,544

[22] Filed: Jul. 18, 1988

[51] Int. Cl.⁶ .................................................. B01D 63/02
[52] U.S. Cl. ............................. 210/321.89; 210/500.23
[58] Field of Search .......................... 210/500.23, 321.89, 210/321.8, 406, 646, 321.79, 321.81, 450

[56] References Cited

U.S. PATENT DOCUMENTS 3,536,611  10/1970  De Filippi et al. ............ 210/321.89 X
4,231,871  11/1980  Lipps et al. ...................... 210/500.32 X
4,689,255  8/1987  Smoot et al. ................... 210/321.89 X

OTHER PUBLICATIONS

Brochure distributed by Asahi Medical Co., Ltd. depicting "Plasmaflo Asahi Plasma Separator".

Primary Examiner—Frank Spear
Attorney, Agent, or Firm—Trask, Britt & Rossa

[57] ABSTRACT

A filter for use in the extracorporeal sampling of blood plasma is disclosed. The filter comprises a housing, an inlet, an outlet, and a sampling port and contains at least a hollow semi-permeable filter fiber through which blood plasma, but not whole blood, may pass. The filter may further comprise analyzing means in communication with the plasma which has passed through the filter fiber for analyzing the plasma. A method of using the filter and a method for making the component of the filter are also disclosed.

1 Claim, 4 Drawing Sheets

FILTER FOR ON-LINE PLASMA SAMPLING

BACKGROUND

1. Field

This invention relates generally to filters. It is particularly directed to a filter device useful for sampling the blood plasma of a dialysis patient.

2. State of the Art

A heterogeneous fluid is a fluid consisting of dissimilar ingredients or constituents. Whole blood, an example of a heterogeneous fluid, consists of specialized cellular elements and a liquid, plasma, in which they are suspended.

Oftentimes, a need exists to sample and analyze the plasma constituent of blood without affecting the other constituents. For example, end stage renal disease ("ESRD") patients undergoing maintenance hemodialysis treatments at home presently send blood samples to laboratories for analysis. The blood sample is analyzed for general chemistry profiles (e.g. electrolyte, plasma hemoglobin, total protein, albumin, and immunoglobin concentrations). Sending out blood samples is tedious and involves a significant loss of the ESRD patient's blood cells. Since ESRD patients are typically anemic, a further loss of red blood cells compounds their anemic condition.

Presently, ESRD patients either ignore the problem of further blood cell loss altogether, or endure a complicated procedure whereby the blood cells withdrawn with a sample are salvaged. To salvage the blood cells, a blood sample is first taken from the patient using a syringe under sterile conditions. The blood sample is then centrifuged, separating the blood cells from the plasma. The blood cells are reinfused into the patient. The plasma sample may then be analyzed.

Since for a large proportion of diagnostic procedures a plasma sample is all that is necessary, a need exists for an inexpensive means for collecting a plasma sample without contributing to further blood loss of an ESRD patient.

Another instance where it would be desirable to analyze an animal's blood plasma without affecting the remaining constituents of the blood is during open heart surgery. During such surgery, it is often desirable to measure various parameters such as blood gas analysis, electrolyte concentration, or plasma concentration of various therapeutic agents, without contributing to unnecessary blood loss. In instances such as surgery it may be desirable to monitor the patient's plasma chemistry several times or even continuously.

SUMMARY OF THE INVENTION

The invention includes an extracorporeal plasma filter. The filter is structured to permit particularly advantageous sampling procedures of portions of heterogeneous fluids. The invention also embraces a method of making a portion of the filter.

The filter includes an elongate housing having an inlet, an outlet, and a sampling port. The housing contains a filter fiber bundle including at least one hollow filter fiber with a first open end, a second open end, and an intermediate semi-permeable wall portion proximate, or in communication with, the sampling port. The first and second open ends are sealably mounted within the housing at the inlet and outlet respectively. The housing encloses a volume around the intermediate portion of the filter fiber bundle. The filter is constructed so that a heterogeneous fluid, such as blood, entering the inlet passes into the first open end of the hollow filter fiber and through the fiber. A portion of the fluid (e.g. a filtrate or diffusate) permeates the semi-permeable portion of the fiber to collect within the housing. The collected portion may then be sampled from the sampling port.

The filter will usually be structured with a plurality of hollow fibers comprising a filter fiber bundle. These fibers are attached one to another near their respective ends, e.g. by gluing. In the mid-portion of the bundle between the respective ends no glue is present, and the individual fibers are unattached. The hollow fibers are placed within a housing, and at least one of the hollow fibers has a semi-permeable mid-portion. A sampling port communicates with the interior of the housing in the vicinity of the semi-permeable portion of the fibers comprising the filter fiber bundle. An inlet is arranged to direct fluid from outside the housing to a first end of the housing. Fluid introduced into the filter passes through the inlet, enters the ends of the individual fibers of the filter fiber bundle at the first end of the housing, and passes through the opposite ends of the fibers. An outlet is arranged at the opposite, or second, end of the housing to receive fluid dialysate passing through the filter fiber bundle and to direct that fluid dialysate to a location exterior the filter.

Fluid directed through the inlet flows through the hollow fibers having a semi-permeable portion. The filtrate passes through the semi-permeable portion of the fibers, and the remaining fluid (i.e. the fluid dialysate) passes through the hollow fibers and through the outlet to exterior the extracorporeal plasma filter. Such an arrangement permits the filtrate to be sampled from the sampling port.

In one embodiment of the invention, ion selective electrodes are associated with the housing or sampling port. The electrodes are placed within the housing to allow testing of the plasma contained therein. Through such a placement, the plasma can be analyzed and monitored continuously.

The invention also includes a method of extracorporeally obtaining a sample of blood plasma from an animal. This method comprises: tapping into the circulatory system of the animal, shunting blood from the animal through the previously described extracorporeal plasma filter, taking a sample of the diffusate which has passed through the semi-permeable filter walls (i.e. plasma) and returning the filtered blood to the animal. This method allows for sampling of the blood plasma without significant blood cell loss to the animal.

Those skilled in the art will recognize other possible applications for the filter which will change the choice of filter fiber and housing. For example, other possible applications include plasmapheresis, desalination of water, condensation of milk, dialysis procedures, blood chemistries during open heart surgery, pharmacokinetic studies, dialysis in an intensive care unit, and use for plasma donation in a blood bank.

DETAILED DESCRIPTION OF THE ILLUSTRATED EMBODIMENTS

Figure 1:
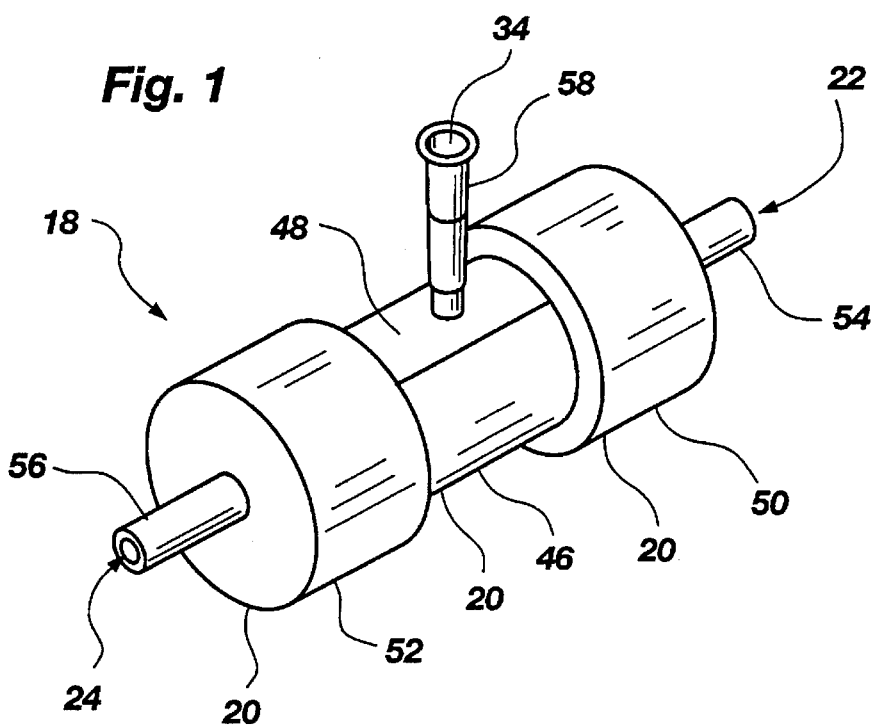
FIG. 1 is a elevational perspective view of a filter of the invention.

The filter 18 (FIGS. 1–4) comprises a housing 20, an inlet 22, an outlet 24, a filter fiber bundle 26 glued or "potted" on both ends 28, 30 leaving a loose mid-portion 32, and a filtrate, diffusate or "sampling" port 34. As illustrated (FIGS. 2 and 4), a receiving chamber 36 and sending chamber 38 are incorporated into the filter to obtain a more uniform flow of a fluid to be passed through the filter 18 through the filter fiber bundle 26. If the fluid is blood, less cell damage occurs due to this uniform flow of fluid through the filter 18.

The housing 20 of the filter is preferably made of a material compatible with both the fluid to be transported through the filter fiber bundle 26, and with the remaining components of the filter 18. If blood is the fluid to be transported through the filter fiber bundle 26, biocompatible materials, such as polycarbonate, acrylic or polyurethane, produce satisfactory results as housing materials. For other applications, materials such as a glass, plastic or metal may be used. The housing 20 is sized and shaped to enclose the filter fiber bundle 26.

Figure 4:
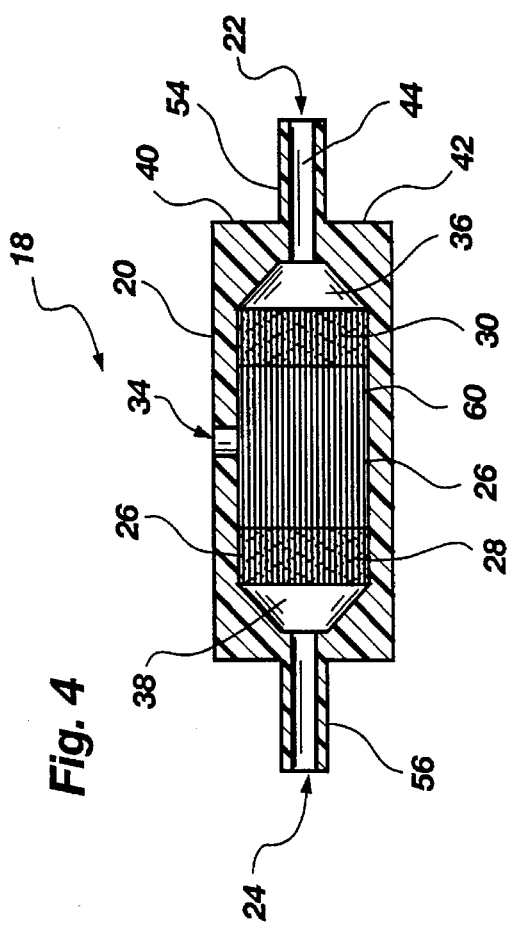
FIG. 4 is a side schematic view of an integrally formed filter.

Referring to FIG. 4, the housing 20 comprises an upper part 40 and a lower part 42 which are joined along seam 44. The upper part 40 contains the filtrate port 34. The inlet 22 and outlet 24 ports are formed by connecting the upper 40 and lower 42 parts of the embodiment depicted in FIG. 4.

Figure 2:
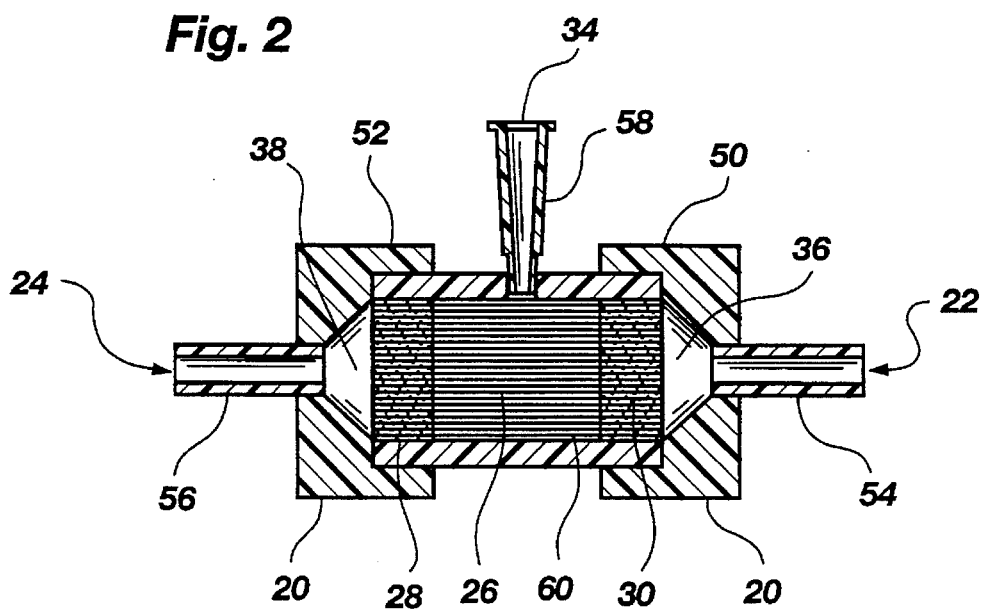
FIG. 2 is a side schematic view of the filter of FIG. 1.
Figure 3:
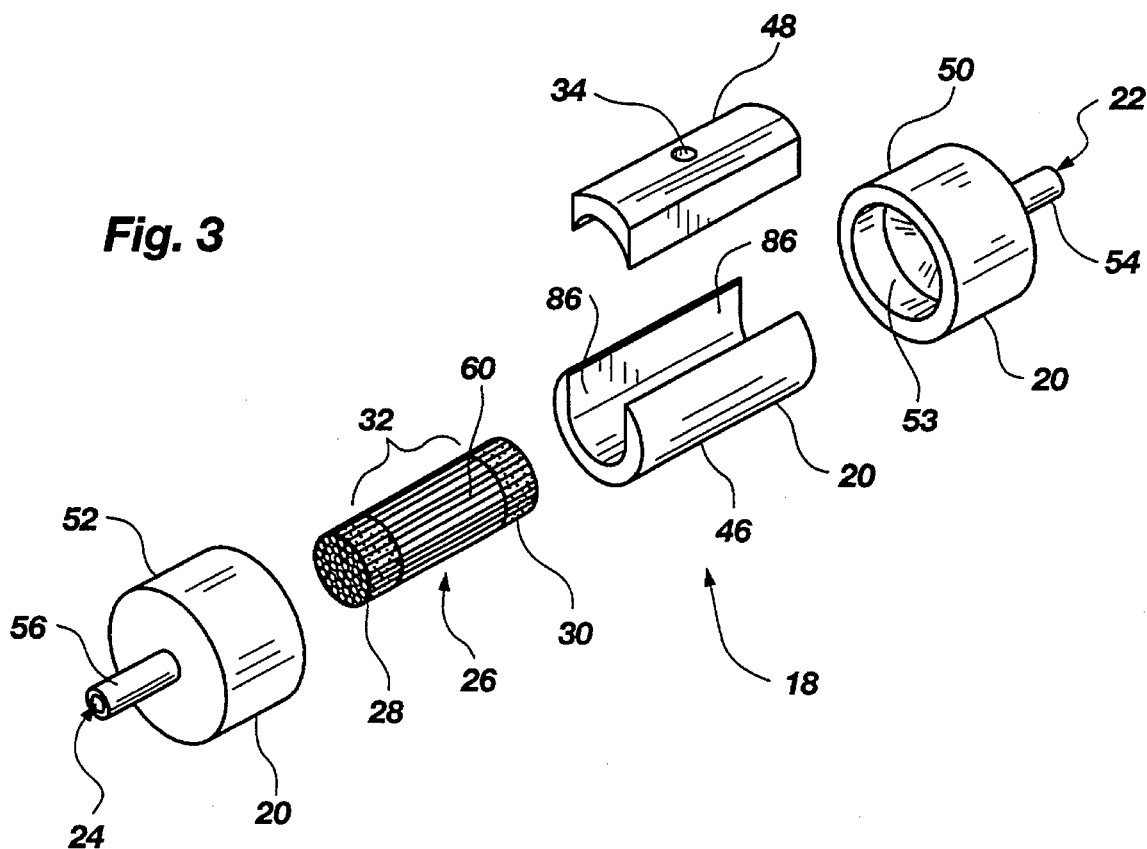
FIG. 3 is an elevational perspective view of the filter of FIG. 1 broken up into its various components.

In the preferred embodiment depicted in FIGS. 1–3, the housing 20 of the filter comprises various interconnecting components. One component is the C-shaped open conduit 46. A top cap 48 is sized and shaped to fit within the open conduit 46 to form an enclosed conduit or pipe (FIG. 1). The filter fiber bundle 26 is lodged within the open conduit 46, and both the open conduit 46 and top cap 48 are sized and shaped to enclose the filter fiber bundle 26 when they are interconnected. The open conduit 46 and top cap 48 may be permanently interconnected by glue or other means. Once interconnected, the open conduit 46 and top cap 48 ("enclosed conduit") are structured to form an air-tight seal around both ends 28, 30 of the potted filter fiber bundle 26 (FIG. 2). In the depicted embodiment, the filtrate port 34 is shown as an aperture in the top cap 48 although such a placement is not necessary. It is only important that the filtrate port 34 be near or communicate with the semi-permeable portion 32 of the filter fiber bundle 26 so that diffusate samples may be taken from the filtrate port 34.

The embodiment depicted in FIGS. 1–3 is preferred for, among other things, ease in manufacturing. With this embodiment, filter fiber bundles 26 comprised of different fibers 60 and adhesives may be used without changing the housing 20. The fibers 60 and adhesive are selected for their compatibility in the particular process they are to be used in.

The depicted filter fiber bundle 26 (FIG. 3) comprises a plurality of hollow filter fibers 60 rolled or connected into a bundle which are "potted" or glued on the bundle's ends 28, 30. Even after the hollow filter fibers are potted, a number of them must have open ends to allow fluid to pass into and out of the filter fibers. The number of filter fibers 60 used in the bundle 26 is dependent upon the pressure decrease which can be tolerated from the inlet port 22 to the outlet port 24. The greater the number of fibers, the smaller the pressure decrease. At least one of the fibers will have a semi-permeable portion, allowing a constituent of the fluid transported through the fiber bundle 26 to pass through the fiber as a filtrate or diffusate to be collected at the sampling port 34.

The choice of filter fiber depends on the intended use of the filter. In the case of a filter to be used as a means of obtaining a plasma sample for laboratory tests, the fluid to pass through the filter fiber bundle 26 is whole blood, and the diffusate or filtrate is blood plasma ("plasma"). Ideal filter fibers allow the plasma to pass through as a filtrate, but do not allow blood cells to pass through their walls. The pressure decrease in between the inlet 22 and outlet 24 ports in this case should be less than about 10 mm Hg. The surface area of the semi-permeable walls of the filter fibers 60 will typically range from about 10 to about 500 square centimeters, and the number of hollow fibers enclosed within the housing will range from about 200 to about 800 fibers. The length of each of the hollow fibers preferably ranges from about 1 to about 3 centimeters. Fibers which have produced satisfactory results in plasma filtration include Enka AG membrane from West Germany, Travenol plasma filtration membranes, and PlasmaPhan membranes. These membranes have semi-permeable portions with average pore sizes of 0.15 to 0.23 microns in the semi-permeable portions.

As depicted in FIGS. 1–3, an inlet end cap 50 and an outlet end cap 52 are placed on both ends of the enclosed conduit. The end caps 50, 52 are sized and shaped to enclose the enclosed conduit containing the filter fiber bundle 26 (FIG. 2). The depicted end caps 50, 52 have a concave inner portion 53, so as to form a receiving chamber 36 and sending chamber 38 of the filter when interconnected with the enclosed conduit containing the filter fiber bundle 26 (FIG. 2). The end caps 50, 52 of the depicted embodiment contain their respective inlet 22 and outlet 24 ports.

The inlet 22 and outlet 24 ports are sized to attach to conduit (e.g. conduit or tubing containing arterial blood from auxiliary circulatory path means, e.g., a blood pump in a hemodialysis procedure (FIG. 6)). The inlet port 22 allows for fluid flow from exterior the filter 18 to the receiving chamber 36. The outlet port 24 allows fluid (e.g unfiltered fluid of dialysate) to pass from the sending chamber 38 to exterior the filter. In the depicted embodiments (FIGS. 1–4), the inlet 22 and outlet 24 ports are interchangeable, and fluid can flow through the filter in either direction. The inlet 22 and outlet 24 ports may have extenders 54, 56. These extenders 54, 56 may be made as integral parts of the housing 20 (FIG. 4) or the end caps 50, 52 (not shown), or may be a separate component sized to fit within the inlet 22 and outlet 24 ports (FIG. 2). The extenders 54, 56 are sized and shaped to connect with whatever conduit is used to connect the filter. These ports 22, 24 may also have Luer-lock® associated therewith (not shown).

The filtrate or "sampling" port 34 is similar to the inlet 22 and outlet 24 ports, and may be placed in the housing 20 at a location proximate the loose mid-portion 32 of the filter fiber bundle 26. Samples of resulting filtrate may be withdrawn from the filter through the sampling port 34 as previously described. An extender 58 (FIGS. 1 and 2) may also be placed in the filtrate port 34. When the filter is used in a hemodialysis procedure (FIG. 6), the extender 58 will typically be of a length that allows for insertion of a needle from a needle-bearing syringe (not shown) to withdraw a sample of the filtrate (i.e. plasma) from the filtrate port 34 without penetrating or otherwise damaging any of the hollow filter fibers of the fiber bundle 26. In the case of a plasma sampling procedure, such an arrangement allows for withdrawal of the plasma sample without damaging the filter fiber bundle 26, thus, preventing blood cell loss through any of the fiber walls.

Figure 7:
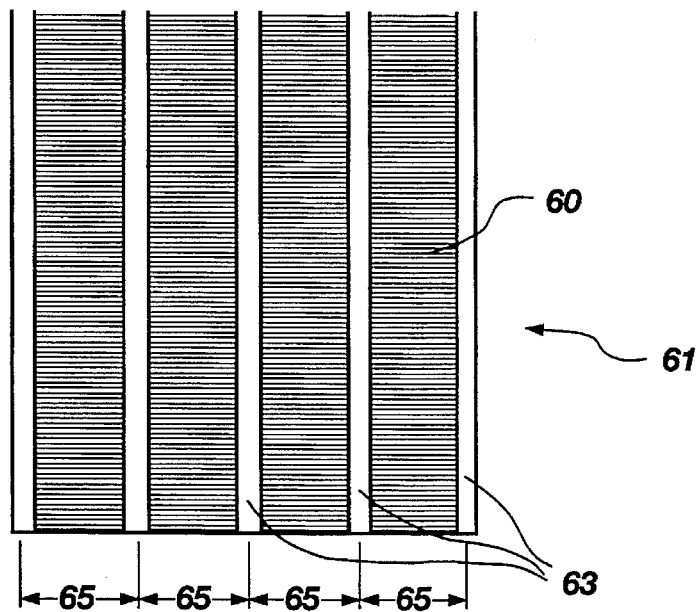
FIG. 7 shows the first step of filter making (laid out fibers).

The filter fiber bundle 26 may be made by the following steps. First, a number of fibers 60 are laid out next to each other in a plane (FIG. 7). The fibers are parallel and touch each other. The number of fibers chosen depends upon the number of fibers desired in the resulting filter fiber bundle, although this particular method works best when the number of fibers exceeds 1000. The laid out fibers may then be sewed to one another if desired. The fibers should be of equal length. The length chosen is preferably a multiple of the desired length of filter fiber bundle.

Second, adhesive is applied to the "mat," generally 61, of fibers in bands 63. The centers of the bands are spaced apart by the length 65 of the desired filter fiber bundle 26, so as to fit within the desired housing 20. The adhesive is applied so that each fiber has some adhesive applied to it. The width of the adhesive bands will preferably be twice that of the glued portions of the filter fiber bundles 26 with the loose portions of fibers in between the bands. The loose portions will be of a width analogous to the loose mid-portion 32 of the filter fiber bundle 26. Adhesive is preferably applied to both sides of the mat.

Third, the mat is rolled manually into a tight fiber bundle, and may be enclosed in a polycarbonate shell. While in this shell, the adhesive is allowed to cure or "dry."

Once dried, the tight fiber bundle is cut or sheared at the center of each of the adhesive bands 63 to form filter fiber bundles 26.

Figure 5:
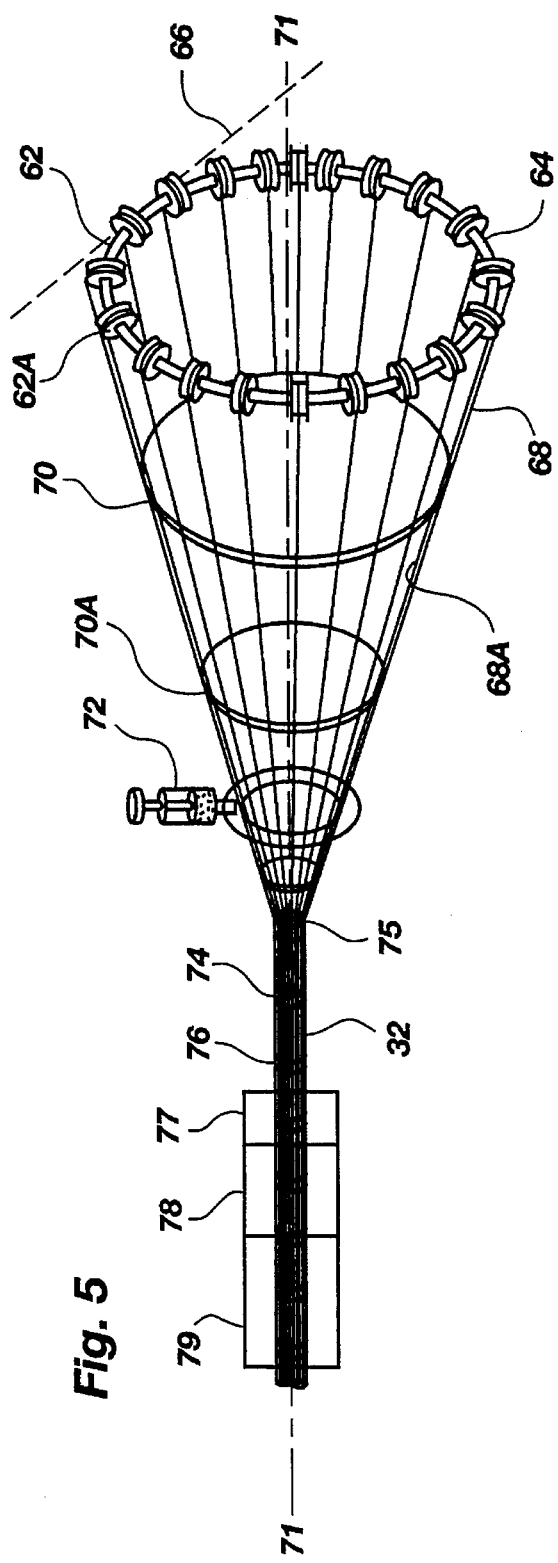
FIG. 5 is a stylized view of an apparatus for making glued bundles of hollow filter fibers.

The invention also embraces an apparatus for manufacturing the filter fiber bundle (FIG. 5). This apparatus includes storage means for holding a plurality of hollow filter fibers. Preferably such means are a plurality of spools 62 or bobbins. Wrapped around each of the spools 62, 62A is at least one hollow filter fiber. The fibers from the spools are directed through guide means. Guide means may be a series of concentric rings 70, 70A arranged linearly about an axis 71 extending away from the storage means 62. Each successive ring has a smaller diameter as it is placed further from the storage means bringing the fibers closer together. Near the last ring, means for administering potting adhesive 72 onto each fiber at preselected increments along the filter fibers is provided. Means for bringing together or adjoining the fibers to form a bundle of filter fibers is supplied. The bundle of filter fibers may then be placed within the extracorporeal plasma filter and then cut or sheared in the center of the glued portion. The cutting of the fibers will usually take place after the potting adhesive was cured or dried.

The spools 62, 62A may be placed on a hoop or ring 64 so that they may rotate about their axis 66 on the ring 64. Each spool 62 is wrapped with up to about twenty-four hollow fibers 60, some of which may be filter fibers (i.e., fibers having a semi-permeable portion). The fibers are brought together into small bundles 68, 68A. The small bundles 68, 68A are led through a series of successively smaller rings 70, 70A, concentric about imaginary axis 71, past a device 72 for administering potting adhesive (e.g. silicone or polyurethane glue) to each hollow filter fiber 60 led past it. The small bundles 68 are led further to means for drawing the small bundles 68, 68A together to form a larger bundle 74 (a "bundler"). The bundler may be another ring 75 of a diameter slightly larger than the larger bundle 74. Bundles are enclosed in the filter housing 20 (FIG. 3). Means for curing the potting adhesive (e.g. heating element) and cutting (e.g. knife blades) the larger bundle 74 at the potted areas 76 may be provided. Means for pulsing the device 72 for administering potting adhesive at preselected intervals along the bundle may also be provided. The preselected intervals are spaced so as to form the loose mid-portions 32 of the fluid fiber bundle 26.

The apparatus for making the filter fiber bundles 26 is put into operation as hereinbefore described. Any number of spools 62 can be accommodated, the only limitation being the size of the facility housing the apparatus. However, generally less than twenty spools will suffice for most applications. Free ends of the small bundles 68, 68A of hollow filter fibers 60 are led through the rings 70, 70A past the adhesive administering device 72, through the bundler 75, and onto some sort of drawing device 77 (e.g. a sheave, a drum or other tension device for drawing the fiber 60). The apparatus is started, and as the small bundles 68, 68A are guided closer together, adhesive is applied onto each fiber 60 at pre-selected lengths so as to form loose mid-portions 32 in the large bundle 74 of hollow filter fibers 60. The potted bundle can then be enclosed in the housing 20 (FIG. 3). The potting adhesive ("glue") can then be cured by a heating device 78 to enhance drying if necessary. Curing means is any device which hastens the drying of the glued portion. If the curing means is a heating device 78, it can be any device which will increase the local ambient temperature about the glued areas of the bundle of filter fibers to hasten the speed of drying of the adhesive. For example, a heating coil or some convection heating method will work. After drying, the larger bundle 74 of hollow filter fibers 60 may be either stored or cut by a shearing or cutting device 79. The larger bundle is cut into preselected lengths for use as filter fiber bundles 26. Typical cutting devices 79 include blades.

Alternatively, the filter fiber bundles 26 may be cut into their preselected lengths, and then incorporated into the filter as shown in FIG. 3. In any event, once placed, the end caps 50, 52 are glued to the other portions 46, 48 of the housing 20.

For filters requiring 10,000 or more fibers, a different method of potting the hollow fibers is preferred. First, the fibers are placed within an appropriately sized C-shaped open conduit 46 (FIG. 3). The length of these fibers will generally exceed the length of the conduit 46 by about 15%. The top cap 48 is then placed to encase the fibers. One end of the fibers is then cut with a blunt shearing blade or scissor. When the hollow fibers are cut with such a blunt device, the open ends of the hollow fibers close. A glue cap or end cap 50 is then placed over the cut end of the encased fibers. Potting glue (e.g. two component polyurethane adhesive sold by Hartel Plastics of California) is injected into the cap through the inlet 22. Sufficient glue to "pot" the fibers is injected, i.e. sufficient glue to prevent fluid from accessing the loose mid-portion of the bundle. The potting glue is allowed to cure. Once the glue is cured, the other end of the fibers may be potted following the aforementioned procedure. The glue caps are then removed or cut off. Cutting is preferred so as to remove the end portion of the fibers leaving open, potted fibers on each end. The end caps 50, 52 to be used with the filter are then placed on the filter to complete the housing.

Figure 6:
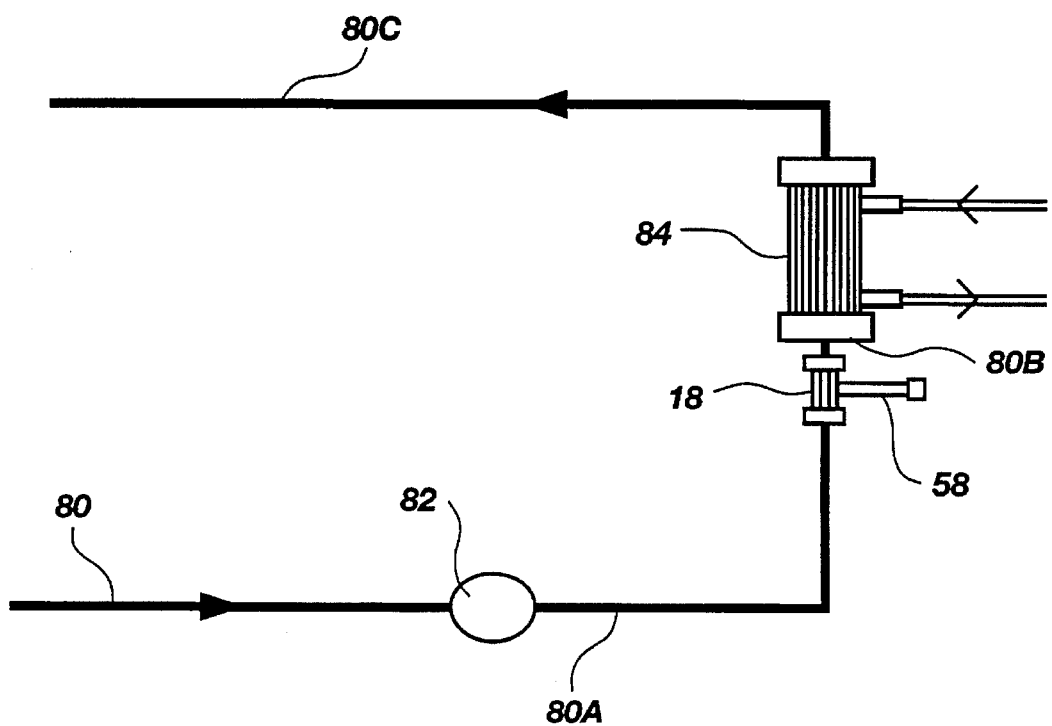
FIG. 6 is a stylized flow sheet showing use of the filter in a hemodialysis procedure.

Once made, the filters have various applications. As shown in FIG. 6, the filter 18 can be incorporated into a hemodialysis procedure. A cannula or catheter (e.g. Travenol® dialysis catheter, 18 gauge) is placed into a hemodialysis patient's artery. Blood from the artery is directed from the patient through the inside of conduit 80 to blood pump 82. Blood pump 82 directs the arterial blood further along the conduit 80A to inlet port 22 (FIGS. 2 and 4) of the filter 18. The blood enters inlet port 22 and progresses to receiving chamber 36. Once in receiving chamber 36, the blood, due to the pressure from the blood pump 82, is forced against the potted area 30 of the filter fiber bundle 26. Since the only openings existing are the entryways into the hollow filter fibers 60, the blood enters into the open ends of one of the hollow filter fibers 60. As the pressurized blood courses through the hollow filter fibers 60, the pressure forces a constituent of the blood (i.e. the plasma) to permeate through the semi-permeable portion of the hollow filter fibers at the loose mid-portion 32 of the filter fiber bundle. The remaining blood dialysate and any unfiltered blood which passed through impermeable fibers passes through the remainder of the filter fiber bundle 26, through the conduit 80B, a dialyzer 84, and is returned through conduit 80C to the patient's circulatory system (FIG. 6).

In safe operating condition, the procedure depicted in FIG. 6 produces 2 to 10 milliliters of plasma as filtrate in approximately 2 to 3 minutes without causing hemolysis, infection or blood cell loss. Of course, as in all procedures involving blood, sterile procedures must be maintained.

In one preferred embodiment, electrodes or other analyzing means 86 are placed within the housing 20 in association with the area where the filtrate will collect in the housing (FIG. 3). The analyzing means are then connected to an apparatus for interpreting the data sent by the analyzing means (e.g. an electronic pH meter (not shown) if the electrodes are useful in measuring pH). Such a placement of analyzing means 86 allows for continuous monitoring of the filtrate, allowing for instantaneous analysis of the filtrate. The analyzing means may be placed in the filtrate port 34 (not shown) or the filtrate port 34 can be used as a drainage port to allow the older filtrate samples to drain off, thus allowing monitoring of newer filtrate samples.

Examples of analyzing means include Clark electrodes for oxygen content measurement of plasma, glucose sensors, chem FET electrodes, and pH electrodes for measuring the pH of the filtrate.

Reference herein to specific details or certain embodiments is not intended to limit the scope of the appended claims.

What is claimed:

1. A filter for producing 1 to 2 ml per minute of diffusate consisting of:

a filter fiber bundle comprising hollow fibers having ends glued one to another to form a loose mid-portion, said hollow fibers having open ends through which a fluid may pass, said filter fiber bundle being placed within a housing and at least one of said hollow fibers having a semi-permeable portion in proximity of the loose mid-portion;

a sampling port communicating with the interior of said housing proximate said loose mid-portion of said filter fiber bundle;

an inlet arranged to direct fluid from outside said housing to contact the end of said filter fiber bundle and further arranged to pass the fluid into said open ends and through said hollow fibers; and an outlet arranged to receive fluid passing through said hollow fibers to exterior said filter, whereby fluid directed through said inlet flows through the hollow fibers, and one to two milliliters of diffusate from the fluid passes through the semi-permeable portion each minute so that said diffusate may be sampled from said sampling port, and a dialysate and unfiltered fluid passes through said hollow fibers and through said outlet to exterior said filter.

\* \* \* \* \*